US006797853B2

(12) United States Patent
Houzvicka et al.

(10) Patent No.: US 6,797,853 B2
(45) Date of Patent: Sep. 28, 2004

(54) PROCESS OF PARAFFIN HYDROCARBON ISOMERISATION CATALYSED BY AN IONIC LIQUID IN THE PRESENCE OF A CYCLIC HYDROCARBON ADDITIVE

(75) Inventors: Jindrich Houzvicka, Turnov (CZ); John Zavilla, Kokkedal (DK); Konrad Herbst, Kgs. Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 10/662,335

(22) Filed: Sep. 16, 2003

(65) Prior Publication Data

US 2004/0059173 A1 Mar. 25, 2004

(30) Foreign Application Priority Data

Sep. 25, 2002 (DK) ......................................... 2002 01416

(51) Int. Cl.$^7$ .............................. C07C 5/22; C07C 5/27
(52) U.S. Cl. ........................ 585/741; 585/745; 585/748
(58) Field of Search ................................ 585/741, 745, 585/748

(56) References Cited

U.S. PATENT DOCUMENTS 2,934,579 A    4/1960  Serniuk et al. ............. 585/746

*Primary Examiner*—Thuan Dinh Dang
(74) *Attorney, Agent, or Firm*—Dickstein Shapiro Morin & Oshinsky LLP

(57) ABSTRACT

A process for the conversion of linear and/or branched paraffins hydrocarbons, catalysed by an ionic liquid catalyst, in the presence of a cyclic hydrocarbon additive containing a tertiary carbon atom. The presence of the specific hydrocarbon additives influences the reaction mechanism by increasing the selectivity towards the formation of paraffin hydrocarbons with a higher degree of branching.

10 Claims, No Drawings

PROCESS OF PARAFFIN HYDROCARBON ISOMERISATION CATALYSED BY AN IONIC LIQUID IN THE PRESENCE OF A CYCLIC HYDROCARBON ADDITIVE

BACKGROUND OF THE INVENTION AND PRIOR ART

The present invention relates to a process for the isomerisation of paraffin hydrocarbons catalysed by an acidic ionic liquid catalyst in the presence of a cyclic hydrocarbon additive containing a structural entity with a tertiary carbon atom, which improves the selectivity towards the formation of multibranched paraffin hydrocarbons.

Paraffin hydrocarbons with high degree of branching are known to be useful blending components for motor gasoline due to their high octane numbers. Such paraffin hydrocarbon fraction can be produced in an isomerisation process increasing the octane number of the $C_4$–$C_9$ cuts. Isomerisation of $C_4$, $C_5$ and $C_6$ paraffins are common refinery processes based on use of e.g. an acidic Friedel-Crafts catalyst such as $AlCl_3$. Processes including higher fractions ($C_7$ to $C_9$ hydrocarbons) meet with significant difficulties due to low selectivity and low octane number of the once-through products.

Several different concepts based on the use of liquid catalysts, solid catalysts as well as supported catalysts have been reported in connection with paraffin isomerisation. Some references also describe the use of specific hydrocarbon additives to the paraffin feed resulting in a positive effect on the isomerisation reaction, such as reduced catalyst deactivation or higher selectivity towards branched products by limiting the cracking reactions. In the following some applications of such hydrocarbon additives are described.

U.S. Pat. No. 4,035,286 describes the isomerisation of methylpentane in the presence of catalyst systems comprised of a mixture of fluorinated alkane sulphonic acids and antimony pentafluoride, e.g. $CF_3SO_3H$ and $SbF_5$. In this example a mixture of methylcyclopentane and cyclohexane is used as additives to the hydrocarbon feed in order to reduce cracking. The amount of methylcyclopetane/cyclohexane mentioned in the patent is in the range 2 wt % to 30 wt % and preferably from 5 wt % to 15 wt %.

In two articles, (1) "M. Bassir, B. Torck, M. Hellin, Bull. Soc. Chim. Fr., 1987, V.4, pages 554–562", and (2) "M. Bassir, B. Torck, M. Hellin, Bull. Soc. Chim. Fr., 1987, V.5, pages 760–766, respectively, the influence of isobutane as additive on the isomerisation of n-heptane catalysed by a mixture of HF and $SbF_5$ is reported. Both articles mention the use of a feed-mixture of isobutane (40–50 wt %), n-pentane (20–25 wt %), n-hexane (20–25 wt %) and n-heptane (10–20 wt %) concluding that n-heptane is isomerised without any cracking. In the case where the feed is composed of isobutane (40 wt %) and n-heptane (60 wt %), the amount of cracking is limited (in the order of 5 wt %).

U.S. Pat. No. 3,903,196 discloses the use of isobutane as additive in the isomerisation of n-hexane catalysed by a mixture of HF and $SbF_5$ on a solid support like fluorinated alumina. The isobutane concentrations in the hydrocarbon feed are above 25 wt % and preferably above 40 wt %. The presence of the hydrocarbon additive results in a reduced catalyst deactivation.

A different example on the use of hydrocarbon additives to the hydrocarbon feed in the paraffin isomerisation is described in U.S. Pat. No. 3,201,494. In this reference, isomerisation of pentane, hexane and heptane compounds is carried out using hexafluoroantimonic acid as catalyst. Use of isobutane (preferably 5 wt %–25 wt %) has shown increase of the rate of the isomerisation reaction. Furthermore, the deactivation rate of the catalyst can be decreased by adding certain cycloalkane compounds chosen from methylcyclopentane, cyclohexane, methylcyclohexane and ethylcyclohexane (preferably 5 wt %–50 wt %) to the feed.

In U.S. Pat. No. 3,394,202 the same catalyst system, hexafluoroantimonic acid, is described as a supported catalyst concept and used for paraffin hydrocarbon isomerisation. This system has the same advantageous characteristics, when isobutane and cycloalkanes are used as additives to the feed.

A relatively new class of acidic catalysts based on ionic liquids, amongst produced from $AlCl_3$, has recently been described in the literature (P. Wasserscheid, W. Keim, Angew. Chem., Int. Ed., 2000, V. 39, pages 3772–3789; T. Welton, Chem. Rev., 1999, V. 99, pages 2071–2083). This group of compounds also referred to as molten salts are constituted of:

(1) an inorganic anion, typically formed from metal halides, such as $AlCl_4^-$, $Al_2Cl_7^-$ or other inorganic anions ($SO_4^{2-}$, $NO_3^-$, $PF_6^-$, $CF_3SO_3^-$, $BF_4^-$ etc.), and
(2) an organic cation, typically derived from N-heterocyclic or alkylammonium entities.

The melting point of ionic liquids is relatively low and an increasing number of ionic liquids are described with melting points below room temperature. Below some characteristics of ionic liquids are listed:

(1) They have a liquid range of about 300° C.
(2) They are good solvents for a wide range of inorganic, organic and polymeric materials.
(3) They exhibit Brønsted and Lewis acidity as well as superacidity.
(4) They have low or no vapour pressure.
(5) Most ionic liquids are thermally stable up to near 200° C., some ionic liquids are stable at much higher temperature (about 400–450° C.).
(6) They are relatively cheap and easy to prepare and upscale.
(7) They are non-flammable and easy in operation.
(8) They are highly polar but non-coordinating materials.

Ionic liquids most frequently demonstrate Lewis acidic properties once they are formed by metal halides. In many cases, however, the ionic liquids also show strong Brønsted (proton) acidity. The proton acidity may originate both from the cation if it contains a proton at the quarternised N atom or from the anion if it contains protons, for instance in $HSO_4^-$, $H_2PO_4^-$.

Also HCl produced via partial hydrolysis for example of the chloroaluminate anion can explain strong proton acidity of the ionic liquids. Addition of a Brønsted Acid, e.g. $H_2SO_4$, to an ionic liquid containing chloroaluminate anions will also increase the amount of protons in the medium and in the case when the Brønsted Acid reacts with the ionic liquid, HCl is liberated to the medium.

Lewis-acidic properties of ionic liquids are governed by two major factors: (1) the nature of the anion, and (2) the molar ratio of the organic part to the inorganic part (for instance in the case of ionic liquids based on metal halides Me (Hal)$_n$ by the molar fraction of Me (Hal)$_n$). If $X_{Me(Hal)n}$< 0.5, the ionic liquid is called basic; if $X_{Me(Hal)n}$=0.5, this is the case of neutral ionic liquid, and finally if $X_{Me(Hal)n}$> 0.5, the ionic liquid can be classified as acidic or in some cases superacidic.

The effect of superacidity of ionic liquids is quite frequently observed for AlCl$_3$-based compositions. Sometimes this effect is related to the presence of dry HCl in the system, which is dissolved in the ionic liquid. The Hammett function $H_0$ for such systems ($H_0$=−18) indicates superacidic properties of the ionic liquids comparable with those of HF—TaF$_5$ ($H_0$=−16) and "magic acid" HF—SbF$_5$ or FSO$_3$H—SbF$_5$ ($H_0$=−25). All these systems are much stronger acids as compared to the conventional 100% H$_2$SO$_4$ ($H_0$=−12), which marks the border of superacidity. Such ionic liquids are also stronger than the solid superacids like SO$_4$/ZrO$_2$ ($H_0$=−16), H$_3$PW$_{12}$O$_{40}$ ($H_0$=−13.5) or H-Nafion ($H_0$=−12).

Room-temperature ionic liquids are promising media for a wide range of catalytic reactions including downstream oil processing, basic organic synthesis and fine chemicals production. Among these processes of potential commercial interest are various alkylation, oligomerisation and isomerisation reactions (D. Zhao, M. Wu, Y. Kou, E. Min, Catalysis Today, V. 74, 2002, pages 157–189).

DETAILED DESCRIPTION OF THE INVENTION

The object of the present invention is a process for the conversion of linear and/or branched paraffin hydrocarbons, into hydrocarbons with a higher degree of branching.

It has now been found that when the process comprise isomerisation in the presence of a ionic liquid catalyst, the selectivity towards formation of hydrocarbons with a higher degree of branching is considerably increased by adding a cyclic hydrocarbon compound containing a tertiary carbon atom. The presence of the specific hydrocarbon additives influences the reaction mechanism by increasing the selectivity towards the formation of paraffin hydrocarbons with a higher degree of branching. Thus, under appropriate reaction conditions this conversion is leading to paraffin hydrocarbon fraction with higher octane number.

A theoretical explanation on the effect of the cyclic hydrocarbon additive on the isomerisation reaction is given below. The role played by a cyclic hydrocarbon additive like e.g. methyl-cyclo-hexane could optionally be described based on its ability to form stable carbocations in the reaction medium. Tertiary carbocations are much more stable than secondary carbocations, which are much more stable than primary carbocations. Methylcyclohexane contains a structural entity with a tertiary carbon atom, which provides the possibility of forming relatively stable tertiary carbocations. This means that the methylcyclohexane by acting as hydride-transfer agent might be able to scavenge carbocations by delivering hydride to a multibranched carbocation, thus forming a multibranched paraffin hydrocarbon product. In the presence of the cyclic hydrocarbon additives, formation of the multibranched paraffin hydrocarbon products is thus favoured over heavy compounds and cracking products resulting in a higher selectivity towards the desirable multi-branched paraffins. The carbocation formed by hydride abstraction from methylcyclohexane might then afterwards be able to abstract hydride from e.g. a methylhexane compound, which then can isomerise to a more branched compound.

The cyclic hydrocarbon compounds used as additives in the isomerisation of paraffin hydrocarbons can be chosen among mono-cyclic, bi-cyclic and poly-cyclic compounds with varying ring sizes, degree of branching and number of alkyl substituents.

The cyclic hydrocarbon compounds, useful as additives, are not limited to compounds containing a tertiary carbon atom. Also compounds, which in the reaction medium are transformed to a compound containing a structural unit with a tertiary carbon atom, can be used as additives e.g. cyclohexane, which under certain conditions will isomerise to methylcyclopentane, thus providing a compound with a tertiary carbon atom.

The cyclic hydrocarbon additives might be used alone or together with other additives.

The ionic liquids used for the hydrocarbon isomerisation reaction represent salts formed by an organic cation such as N-containing heterocyclic or N-containing aliphatic moiety and an inorganic anion, which may be an anion derived from metal halides or mixed metal halides. The cation may be an alkyl substituted pyridinium, piperidinium, quinolinium (or similar amine compounds) with one or several alkyl or aryl groups or an alkyl ammonium (mono, di, tri or tetra-alkyl ammonium compound). The anion may be derived from any metal halide with strong Lewis acidic properties for instance AlCl$_4^-$, AlBr$_4^-$, GaCl$_4^-$, Al$_2$Cl$_7^-$, Al$_2$Cl$_6$Br$^-$ and the like. The ionic liquid chosen for paraffin isomerisation may be characterised by the amine:Lewis acid molar ratio from 1:3 to 2:1, more preferably from 1:2.5 to 1:1.

The ionic liquid catalyst may be used alone or in combination with a metal salt additive or a Brønsted Acid. The metal salt additive can be chosen from compounds containing a metal cation chosen from group 4, 6, 8, 11 or 12 (using current IUPAC nomenclature for the Periodic Table of elements with groups from 1–18), e.g. Mo(V), Fe(III) or Cu(II).

The Brønsted Acid can be chosen from HCl, CF$_3$SO$_3$H, ClSO$_3$H, H$_2$SO$_4$, H$_3$PO$_4$ and the like.

Physical mixtures of several of these additive compounds may also be used.

The solubility of hydrocarbons in ionic liquids is limited and for instance paraffins and naphthenes are generally immiscible with ionic liquids. Olefins and aromatic compounds demonstrate a clear dependence of the solubility on the oleophilic properties of the ionic liquid. The longer the chain length of the radical attached to the N-heterocyclic moiety, the higher the solubility of olefins and aromatics in the ionic liquids. However, most of the commonly used organic solvents and reagents are immiscible with ionic liquids. This simplifies the use of ionic liquids in a biphasic system and provides a procedure for a simple product/catalyst separation.

Paraffin isomerisation can be carried out in pressurised equipment under high pressure or in a glass vessel at atmospheric pressure. The pressure in the autoclave can be varied from 1 bar to 60 bar. Any gas like helium, argon, nitrogen, hydrogen or dry air can be used in the reaction. The reaction temperature can vary in a range from −30 to 150° C. Temperatures out of this range can also be used, although they are less preferred.

Linear n-paraffins such as n-butane, n-pentane, n-hexane, n-heptane, n-octane, n-nonane and monomethyl-alkanes such as e.g. 2- and 3-methylhexane or a mixture thereof can be used as substrates of the isomerisation process forming a product containing paraffin hydrocarbons with a higher degree of branching.

In this disclosure different hydrocarbon feeds have been used for the isomerisation experiments as specified in the examples.

EXAMPLES

Example 1

In an inert atmosphere ($N_2$) trimethylamine hydrochloride (39.13 g, 0.409 mole) is added to aluminium chloride (98.28 g, 0.737 mole). The light-brown viscous melt which forms is heated to 90° C. under stirring and kept at this temperature for 2 hours. From the resulting liquid may precipitate some solid $AlCl_3$ after cooling to room temperature. In the isomerisation experiments described below, only the liquid phase has been used as catalyst. The ionic liquid can be stored in inert atmosphere ($N_2$) without decomposition.

Example 2

Feed A:

No cyclic hydrocarbon additive present.

24.4 wt % n-heptane, 33.0 wt % 2-methylhexane, 34.9 wt % 3-methylhexane, 2.1 wt % 2,4-dimethylpentane, 3.4 wt % 2,3-dimethylpentane and 2.2 wt % of other $C_7$ isomer compounds.

Initial amount of Multi-branched $C_7$ products: 5.8 wt %.

In an inert atmosphere ($N_2$) an autoclave with mechanical stirrer is charged with 40 ml ionic liquid (56 g) prepared according to Example 1, and 40 ml of the organic hydrocarbon feed containing a certain amount of additive (see Table 1). The system was pressurised with 5 bar helium (for sampling) and afterwards vigorously stirred (600 rpm) at constant temperature. Samples of the hydrocarbon phase are taken at regular intervals and analysed by a gas chromatograph.

Example 3

Feed B:

Additive: Methylcyclohexane.

35.6 wt % methylcyclohexane, 19.5 wt % n-heptane, 20.4 wt % 2-methylhexane, 20.0 wt % 3-methylhexane, 1.0 wt % 2,4-dimethylpentane, 1.5 wt % 2,3-dimethylpentane and 2.0 wt % of other $C_7$ isomer compounds.

Initial amount of Multi-branched $C_7$ products: 2.7 wt %

Experiment performed as described in Example 2.

Example 4

Feed C:

Additive: Dimethylcyclopentane and methylcyclohexane.

7.3 wt % dimethylcyclopentane, 21.3 wt % methylcyclohexane, 13.2 wt % n-heptane, 17.3 wt % 2-methylhexane, 19.3 wt % 3-methylhexane, 4.3 wt % 3-ethylpentane, 2.6 wt % 2,2-dimethylpentane, 4.7 wt % 2,4-dimethylpentane, 1.4 wt % 3,3-dimethylpentane, 5.5 wt % 2,3-dimethylpentane and 3.1 wt % of other $C_7$ compounds.

Initial amount of multi-branched $C_7$ products: 14.8 wt %.

Experiment performed as described in Example 2.

Example 5

Feed D:

Additive: Methylcyclohexane.

35.3 wt % methylcyclohexane, 10.2 wt % n-heptane, 17.9 wt % 2-methylhexane, 16.8 wt % 3-methylhexane, 1.2 wt % 3-ethylpentane, 5.4 wt % 2,2-dimethylpentane, 4.7 wt % 2,4-dimethylpentane, 2.5 wt % 3,3-dimethylpentane, 4.9 wt % 2,3-dimethylpentane and 1.1 wt % of other $C_7$ compounds.

Initial amount of Multi-branched $C_7$ products: 18.2 wt %

Experiment performed as described in Example 2.

Example 6

Feed E:

Additive: Methylcyclohexane.

50.9 wt % methylcyclohexane, 14.9 wt % n-heptane, 15.7 wt % 2-methylhexane, 15.4 wt % 3-methylhexane, 0.8 wt % 2,4-dimethylpentane, 1.1 wt % 2,3-dimethylpentane and 1.2 wt % of other $C_7$ compounds.

Initial amount of Multi-branched $C_7$ products: 2.0 wt %

Experiment performed as described in Example 2.

TABLE 1

| Example | Additive | Amount of additive (wt %) | Temperature (° C.) | Time (min) | Yield of multi-branched isomers (wt-%) | Selectivity (%) |
|---|---|---|---|---|---|---|
| 2 | Feed A: No additive (reference example) | 0 wt % | 50 | 102 | 8.0 | 10.0 |
| | | | | 139 | 8.9 | 11.1 |
| | | | | 199 | 9.7 | 11.4 |
| | | | | 254 | 9.4 | 10.8 |
| 3 a) | Feed B: Containing MCH | 35.6 wt % MCH | 50 | 24 | 7.2 | 95.3 |
| | | | | 39 | 12.0 | 93.9 |
| | | | | 89 | 15.5 | 79.9 |
| | | | | 135 | 16.9 | 61.1 |
| | | | | 188 | 17.5 | 55.7 |
| | | | | 276 | 17.8 | 47.5 |
| 3 b) | Feed B: Containing MCH | 35.6 wt % MCH | 25 | 29 | 3.3 | 96.6 |
| | | | | 58 | 5.5 | 98.0 |
| | | | | 128 | 10.8 | 97.4 |
| | | | | 177 | 15.2 | 95.7 |
| | | | | 265 | 17.7 | 90.0 |
| | | | | 318 | 18.7 | 86.7 |
| | | | | 363 | 19.2 | 82.5 |
| | | | | 403 | 19.7 | 78.4 |
| 4 a) | Feed C: Containing DMCP and MCH | 7.3 wt % DMCP 21.3 wt % MCH | 50 | 34 | 19.9 | 89.0 |
| | | | | 60 | 21.0 | 82.0 |
| | | | | 122 | 21.7 | 67.5 |
| | | | | 179 | 21.8 | 54.0 |
| 4 b) | Feed C: Containing DMCP and MCH | 7.3 wt % DMCP 21.3 wt % MCH | 25 | 34 | 14.9 | 92.5 |
| | | | | 60 | 16.0 | 93.3 |
| | | | | 123 | 20.0 | 92.2 |
| | | | | 181 | 21.7 | 91.0 |
| | | | | 238 | 22.3 | 89.3 |
| | | | | 298 | 23.1 | 83.7 |
| | | | | 380 | 23.4 | 79.3 |
| | | | | 430 | 24.1 | 76.8 |
| 5 a) | Feed D: Containing MCH | 35.3 wt % MCH | 50 | 36 | 23.3 | 86.7 |
| | | | | 59 | 24.5 | 77.6 |
| | | | | 115 | 24.5 | 57.4 |
| 5 b) | Feed D: Containing MCH | 35.3 wt % MCH | 25 | 33 | 18.7 | 98.7 |
| | | | | 68 | 20.3 | 98.4 |
| | | | | 139 | 23.2 | 96.4 |
| | | | | 237 | 25.5 | 90.3 |
| | | | | 304 | 26.0 | 84.5 |
| 6 | Feed E: Containing MCH | 50.9 wt % MCH | 50 | 54 | 9.0 | 93.2 |
| | | | | 124 | 12.3 | 81.7 |
| | | | | 180 | 14.1 | 67.7 |
| | | | | 245 | 14.5 | 61.9 |

DEFINITIONS
Multi-branched $C_7$ products: Dimethylpentanes and trimethylbutane.
$C_{6-}$ products: Compounds containing six and less than six carbon atoms.
$C_{8+}$ products: Compounds containing eight and more than eight carbon atoms.
Yield of multi-branched $C_7$ products is defined as: Sum of multi-branched $C_7$ products.
Selectivity to multi-branched $C_7$ products is defined as: 100 × (sum of multi-branched $C_7$ products)/(sum of multi-branched $C_7$ products + $C_{6-}$ products + $C_{8+}$ products).

What is claimed is:

1. Process for isomerisation of paraffin hydrocarbons catalysed by an ionic liquid catalyst in the presence of one or more cyclic hydrocarbon additives in a reaction medium, which cyclic hydrocarbon additives contain and/or are transformed in the reaction medium to a compound containing a structural unit with a tertiary carbon atom.

2. A process according to claim 1, wherein the cyclic hydrocarbon additive is chosen among compounds containing from 6 to 8 carbon atoms.

3. A process according to claim 1, wherein the cyclic hydrocarbon additive is chosen from methylcyclohexane, dimethylcyclopentane or mixtures thereof.

4. A process according to claim 1, wherein the ionic liquid catalyst comprises an N-containing heterocyclic and/or aliphatic organic cation and an inorganic anion derived from metal halides or mixed metal halides.

5. A process of claim 1, wherein a cation of the ionic liquid catalyst is an N-aliphatic moiety with one or more alkyl or aryl groups.

6. A process of claim 5, wherein the N-aliphatic moiety is an ammonium compound and/or an alkyl substituted pyridinium, piperidinium or quinolinium compound.

7. A process of claim 1, wherein the anion of the ionic liquid is derived from a metal halide with strong Lewis acidic properties.

8. A process of claim 1, wherein the ionic liquid catalyst is obtained by combining N-containing heterocyclic and/or N-containing aliphatic organic compounds with one or more metal halides in a molar ratio of between 1:3 and 1:0.5.

9. A process of claim 4, wherein the metal halide is selected from $AlCl_4^-$, $AlBr_4^-$, $GaCl_4^-$, $Al_xCl_{3x+1}^-$, $1<x<2$ and $Al_xCl_{3x}Br^-$, $1<x<2$.

10. A process of claim 1, wherein the isomerisation is performed at a pressure from 1 to 60 bar and a temperature from −30 to 150° C. and a hydrocarbon feed:catalyst volume ratio is from 20:1 to 1:20.